US010144718B2

(12) United States Patent
Engendahl et al.

(10) Patent No.: US 10,144,718 B2
(45) Date of Patent: Dec. 4, 2018

(54) CONTINUOUS HYDROGENATION OF LEVULINIC ACID

(71) Applicant: DSM IP ASSETS B.V., Heerlen (NL)

(72) Inventors: Barthel Engendahl, Echt (NL); Roel Wim Wiertz, Echt (NL); Jan Van Der Spoel, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/551,133

(22) PCT Filed: Feb. 16, 2016

(86) PCT No.: PCT/EP2016/053254
§ 371 (c)(1),
(2) Date: Aug. 15, 2017

(87) PCT Pub. No.: WO2016/131821
PCT Pub. Date: Aug. 25, 2016

(65) Prior Publication Data
US 2018/0022721 A1 Jan. 25, 2018

(30) Foreign Application Priority Data
Feb. 18, 2015 (EP) .................................. 15155585.1

(51) Int. Cl.
C07D 307/33 (2006.01)
B01J 21/18 (2006.01)
B01J 21/06 (2006.01)
B01J 23/46 (2006.01)
B01J 35/00 (2006.01)

(52) U.S. Cl.
CPC .......... C07D 307/33 (2013.01); B01J 21/063 (2013.01); B01J 21/18 (2013.01); B01J 23/462 (2013.01); B01J 35/0006 (2013.01)

(58) Field of Classification Search
CPC ....... C07D 307/33; B01J 21/063; B01J 21/18; B01J 23/462; B01J 35/0006
See application file for complete search history.

(56) References Cited

U.S. PATENT DOCUMENTS

| 4,897,497 | A | 1/1990 | Fitzpatrick |
| 5,608,105 | A | 3/1997 | Fitzpatrick |
| 6,054,611 | A | 4/2000 | Farone et al. |
| 8,138,371 | B2 | 3/2012 | Fitzpatrick |
| 2003/0055270 | A1 | 3/2003 | Manzer |
| 2004/0254384 | A1 | 12/2004 | Manzer et al. |
| 2010/0312026 | A1 | 12/2010 | Lake et al. |
| 2010/0324310 | A1 | 12/2010 | Dumesic et al. |
| 2012/0302766 | A1 | 11/2012 | Dumesic et al. |
| 2012/0329981 | A1* | 12/2012 | Castelijns ............ C07D 307/33 528/335 |

FOREIGN PATENT DOCUMENTS

| CN | 102658131 | 9/2012 |
| WO | WO 2012/175439 | 12/2012 |
| WO | WO 2014/056486 | 4/2014 |

OTHER PUBLICATIONS

International Search Report for PCT/EP2016/053254, dated Jul. 28, 2016, 4 pages.
Manzer, "Catalytic synthesis of α-methylene-γ-valerolactone: a biomass-derived acrylic monomer", Applied Catalysis A: General, vol. 272, No. 1 (2004), pp. 249-560.
Mehdi et al. "Integration of homogenous and heterogeneous catalytic processes for a multi-step conversion of biomass: from sucrose to levulinic acid, valerolactone, 1,4-pentanediol, 2-methyltetrahydrofuran, and alkanes", Topics in Catalysis, Kluwer Academic Publishers—Plenum publishers, NE, vol. 48, No. 1-4, Apr. 5, 2008, pp. 49-54.
Chalid et al: "Experimental and kinetic modeling studies on the biphasic hydrogenation of levulinic acid to [gamma]-valerolactone using a homogeneous water-soluble Ru-(TPPTS) catalyst", Journal of Molecular Catalysis A: Chemical, vol. 341, No. 1-2, May 1, 2011, pp. 14-21.
D. J. Hayes et al., The Biofine Process—Production of Levulinic Acid, Furfuraldehyde, and Formic Acid from Lignocellulosic Feedstocks, in Biorefineries—Industrial Processes.
B. Kamm et al., eds Products, Status Quo and Future Directions,., Wiley-VCH, Weinheim, Germany, 2010, p. 139-164.

* cited by examiner

Primary Examiner — Timothy R Rozof
(74) Attorney, Agent, or Firm — Nixon & Vanderhye P.C.

(57) ABSTRACT

The invention relates to a continuous or repetitive batch process for the hydrogenation of levulinic acid (LA) or esters thereof to at least gamma valerolactone (GVL) in a reactor comprising a feed stream and an outlet stream, in the presence of a solid Ru catalyst, said process comprising (a) pretreating said solid Ru catalyst with a reductant; and (b) reacting levulinic acid with hydrogen and the pretreated solid Ru catalyst obtained in step (a) at a temperature and residence time suitable to form at least GVL, characterized in that the pretreatment is in the presence of a first solvent which comprises water. This process is stable and little or no Ru will leak form the support.

12 Claims, 2 Drawing Sheets

CONTINUOUS HYDROGENATION OF LEVULINIC ACID

Figure 1:
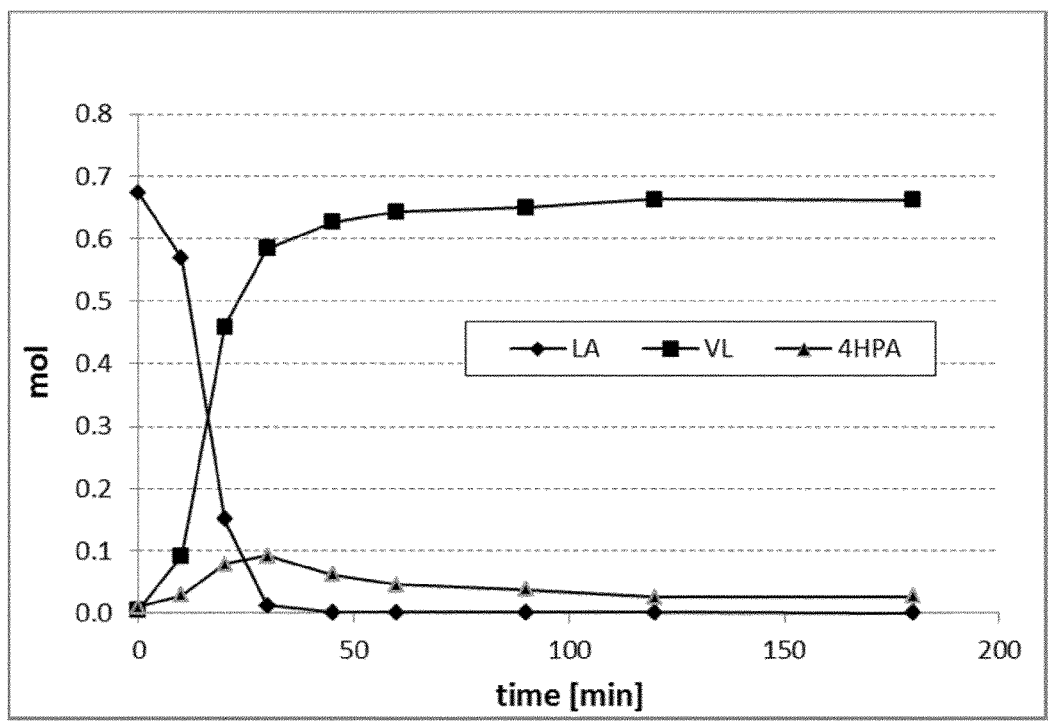

This application is the U.S. national phase of International Application No. PCT/EP2016/053254 filed 16 Feb. 2015, which designated the U.S. and claims priority to EP Patent Application No. 15155585.1 filed 18 Feb. 2015, the entire contents of each of which are hereby incorporated by reference.

FIELD OF THE INVENTION

The present invention relates to a process for the production of valerolactone, to a method to stabilize a solid Ru catalyst for a hydrogenation reaction, and to a Ru catalyst obtainable thereof.

BACKGROUND OF THE INVENTION

Gamma-valerolactone (5-methylbutyrolactone, in the context of the invention also referred to as "valerolactone") is a valuable compound which is inter alia used in the production of adipic acid (1,6-hexanedioic acid) which is an important precursor for inter alia the production of polyamides such as polyamide 6,6 (also referred to as "Nylon") or polyamide 4,6 (also referred to as "Stanyl"). Further, esters of adipic acid may be used in plasticisers, lubricants, solvents and in a variety of polyurethane resins. Other uses of adipic acid are as food acidulants, applications in adhesives, insecticides, tanning and dyeing.

US2003/0055270 discloses a process to produce valerolactone from levulinic acid using a solid Ru catalyst, e.g. supported on carbon. WO2012175439 discloses a process to produce valerolactone from levulinic acid using a solid Ru catalyst, e.g. supported on carbon whereby the hydrogenation reaction is done in the presence of at least 0.08% (w/w) water relative to the amount of levulinic acid. Other references to the hydrogenation of levulinic acid are Hasan Mehdi et al: "Integration of homogeneous and heterogeneous catalytic processes for a multi-step conversion of biomass: from sucrose to levulinic acid, valerolactone, 1,4-pentanediol, 2-methyl-tetrahydrofuran, and alkanes", Topics in Catalysis, Kluwer Academic Publishers—Plenum publishers, NE, vol. 48, no. 1-4, 5 Apr. 2008, pages 49-54; and M. Chalid et al: "Experimental and kinetic modeling studies on the biphasic hydrogenation of levulinic acid to [gamma]-valerolactone using a homogeneous water-soluble Ru-(TPPTS) catalyst", Journal of Molecular Catalysis A: Chemical, vol. 341, no. 1-2, 1 May 2011, pages 14-21.

Levulinic acid (LA) is a starting molecule for the synthesis of commercially important compounds. Commercially, LA is made from furfuryl alcohol. It is also possible to produce LA by acid hydrolysis of biomass although this is not commercially practiced (see for example U.S. Pat. No. 5,608,105, U.S. Pat. No. 8,138,371, US2010/312006, U.S. Pat. No. 4,897,497, U.S. Pat. No. 6,054,611, and "The Biofine Process—Production of Levulinic Acid, Furfuraldehyde, and Formic Acid from Lignocellulosic Feedstocks", D. J. Hayes, S. Fitzpatrick, M. H. B. Hayes, J. R. H. Ross, in Biorefineries—Industrial Processes and Products, Status Quo and Future Directions, B. Kamm, P R. Gruber, M. Kamm, eds., Wiley-VCH, Weinheim, Germany, 2010, p 139-164).

Prior to the hydrogenation reaction the catalyst can be activated by pretreatment with a reductant. US2004/254384 relates to the production of gamma valerolactone from levulinic acid using a solid Ru catalyst. The catalyst is reduced in hydrogen for 2 hours at 400° C. prior to use. In APPLIED CATALYSIS A: GENERAL, vol. 272, no. 1-2, (2004), p. 249-256 is described a repeated batch process for the hydrogenation of levulinic acid into gamma valerolactone using a solid ruthenium catalyst (Ru/C). The catalyst is reduced in hydrogen for 2 hours at 400° C. prior to use. In US2012/302766 is described the hydrogenation of levulinic acid into gamma valerolactone using a solid ruthenium catalyst (Ru—Sn/C) and water as solvent uses a Ru/Sn catalyst. The catalyst is reduced for 3 hours at 723° K (450° C.) before use. In CN102658131A is described the hydrogenation of levulinic acid into gamma valerolactone using a solid ruthenium catalyst and water as solvent. The catalyst is purged with hydrogen for 2 hours before use. US2010/324310 describes a batch process for the hydrogenation of levulinic acid into gamma valerolactone using a solid ruthenium catalyst (Ru/C) and water as solvent. The catalyst is reduced with hydrogen at 673° K (400° C.) before use. All these processes use pre-treatment with $H_2$ in the gasphase at high temperatures which consumes a lot of energy and requires a separate reactor of dedicated design. This invention is aimed at overcoming at least some of these problems.

SUMMARY OF THE INVENTION

The invention relates to a continuous or repetitive batch process for the hydrogenation of levulinic acid (LA) or esters thereof to at least gamma valerolactone (GVL) in a reactor comprising a feed stream and an outlet stream, in the presence of a solid Ru catalyst, said process comprising (a) pretreating said solid Ru catalyst with a reductant; and (b) reacting levulinic acid with hydrogen and the pretreated solid Ru catalyst obtained in step (a) at a temperature and residence time suitable to form at least GVL, characterized in that the pretreatment is done in the presence of a first solvent which comprises water. The pretreatment can be done at low temperatures and the presence of water reduces or even prevents leaching of the catalyst. A preferred reductant is $H_2$. The temperature in step (a) is preferably 350° C. or less, e.g. between 80° C. and 350° C., preferably the temperature is the same as in step (b). The process allows for step (a) and step (b) to be carried out in the same reactor. The first solvent is preferably essentially free of GVL. The hydrogenation reaction is preferably done in the presence of a second solvent, which preferably comprises water, and preferably the first and second solvent are the same. The feed stream preferably comprises levulinic acid and optionally (at least part of) said second solvent. The concentration of the second solvent in the feed stream is preferably 5 wt % less. The hydrogenation reaction is preferably done in the presence of water wherein the steady state concentration of water in the reactor is between 13-20% by wt. The Ru is preferably supported on C or $TiO_2$. The invention also relates to a method to stabilize a solid Ru catalyst, which catalyst is suitable for a hydrogenation reaction, said process comprising contacting the catalyst with a reductant prior to the hydrogenation reaction in a solvent comprising water, and to a solid Ru catalyst obtainable by the claimed method.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

In a first aspect the invention relates to a continuous or repetitive batch process for the hydrogenation of levulinic acid (LA) or esters thereof to at least gamma valerolactone (GVL) in a reactor comprising a feed stream and an outlet stream, in the presence of a solid Ru catalyst, said process comprising (a) pretreating said solid Ru catalyst with a reductant; and (b) reacting levulinic acid with hydrogen and the pretreated solid Ru catalyst obtained in step (a) at a temperature and residence time suitable to form at least GVL, characterized in that the pretreatment is done in the presence of a first solvent which comprises water.

In a continuous process and a repetitive batch process the catalyst remains in the hydrogenation reactor, whilst substrate (levulinic acid) is fed to the reactor, and product (gamma valerolactone) is leaves the reactor.

The conversion of LA or esters thereof to GVL is a hydrogenation reaction. The skilled person knows how to carry out hydrogenation of LA or esters thereof to GVL. For example, US2003/0055270 and describes the hydrogenation of LA to GVL.

The temperature at which the hydrogenation reaction is carried out is not critical and may be anywhere between 100 and 250° C., more preferably between 100 and 200° C. Preferably a temperature of between 100 and 150° C. is used because it seems that the highest selectivity can be obtained in this temperature range. Lower temperatures are also desired due to cost considerations and equipment requirements. A suitable reaction temperature is about 110° C.

The pressure at which the process of the invention is carried out is also not critical, but it may be advantageous to carry out the process at lower pressure, e.g. less than 4.8 MPa. Preferably the pressure is between 1 and 4 MPa, more preferably between 1 and 3 MPa, even more preferably between 1 and 2.5 MPa, even more preferably between 1 and 2.2 MPa.

The amount of catalyst to be used in the hydrogenation reaction is not critical. Typically in a slurry phase hydrogenation process the catalyst contains between 0.1 and 10 wt % (preferably 0.5-5 wt %) Ru and the amount of catalyst including support is generally in the range of 0.1 to 10 wt % (preferably 1-5 wt %) based on the liquid phase present in the reactor. Preferably the amount of Ru is between 2.5 and 2,000 ppm.

The process of the invention may be carried out as a repetitive batch process, or more preferred as a continuous process. The skilled person can simply monitor the (remaining) amount of LA during the course of the hydrogenation reaction and proceed with step (b) until practically all of the LA or ester thereof has been converted.

The reactor for the hydrogenation reactor may be a well-mixed reactor (CSTR, bubble column, etc.) or a staged reactor (multiple CSTR's or bubble columns in series). The hydrogenation reaction is preferably done in the presence of a second solvent. The Ru is preferably supported on C or $TiO_2$.

The hydrogenation may be done with free levulinic acid, or with an ester of levulinic acid. Examples of LA esters are levulinic acid alkyesters, such as levulinic acid methylester or levulinic acid ethylester.

In the process of the invention, prior to the hydrogenation reaction the catalyst is pretreated with a reductant in a solvent, that is, contacted with a reductant. Pretreatment may involve adding a reductant to the catalyst, or vice versa. In the context of the invention the contacting is also referred to as "pre-treatment". The inventors have found that if the catalyst is pretreated in a solvent not comprising any water, a repeated batch or continuous reaction would not be stable. The GVL yield is insufficient, and Ru may leak from the solid support. Any reductant can be used, but a preferred reductant is hydrogen.

The pretreatment of the solid Ru catalyst is done in the presence of a first solvent comprising water.

The first solvent preferably comprises at least 5 wt % water, more preferably at least 10 wt % water, at least 20 wt % water, more preferably at least 30 wt % water, at least 40 wt % water, more preferably at least 50 wt % water, at least 60 wt % water, even more preferably at least 70 wt % water, at least 80 wt % water, even more preferably at least 90 wt % water or at least 95 wt % water, at least 99 wt % water, all based on the total weight of the first solvent, more preferably the first solvent is water.

The first solvent preferably comprises 50 wt % GVL or less, more preferably 20 wt % GVL or less, 10 wt % GVL or less, 5 wt % GVL or less, 1 wt % GVL or less, most preferably the first solvent is essentially free of GVL. The first solvent is also preferably not LA or an ester thereof.

Pretreatment of the solid Ru catalyst can be done in separately from the hydrogenation reaction, e.g. in a reactor. In such configuration the reduced catalyst can be pumped into the hydrogenation reactor.

Alternatively, and preferably, pretreatment of the solid Ru catalyst can be done in the same reactor as the hydrogenation reactor. For example, the hydrogenation reactor can be loaded with catalyst and a first solvent comprising water, reductant (such as hydrogen) is added, and if the pretreatment has reached a desired level the hydrogenation reaction can start.

In both alternatives it is essential that the catalyst is pre-treated with a solvent comprising water before it comes in contact with LA or esters thereof and/or with GVL.

The skilled person can easily establish when the pre-treatment is sufficient, and when the catalyst can be contacted with the LA or esters thereof, in other words, when the hydrogenation reaction can start. This is conveniently done on lab scale, by varying the time, temperature, and reductant concentration (e.g. hydrogen pressure) in the pre-treatment step, such that the subsequent hydrogenation reaction is stable, and/or that there is no or negligible (soluble) Ru leakage.

The pre-treatment conditions are independent of the scale/conditions of hydrogenation reaction. The preferred reductant is hydrogen, because the hydrogenation reaction also involves hydrogen. In this embodiment the hydrogen pressure and/or temperature in the pre-treatment and hydrogenation reaction are the same. If the pre-treatment is done in the hydrogenation reactor, the catalyst can be added to said reactor, typically in the presence of a solvent (to make it transportable), next hydrogen can be added. Then, when the pre-treatment has been carried out, LA or esters thereof can be added to the hydrogenation reactor, preferably ≤5 wt % solvent in the LA stream, even more preferably with no solvent. In the context of the invention, LA or esters thereof is not considered a solvent. This embodiment has additional advantages that there is no reversion, no re-oxidation or deactivation of the catalyst due to contact of oxygen.

The temperature of the pretreatment is preferably done at a temperature of 350° C. or less, more preferably between 80° C. and 350° C., between 80 and 300° C., between 80 and 250° C., between 80 and 200° C., more preferably between 80 and 150° C., more preferably between 90 and 130° C., even more preferably between 100 and 120° C.

Preferably the temperature in step (a) is the same as the temperature in step (b), for reasons of process simplicity and energy cost. This is especially advantageous when step (a) and step (b) are carried out in the same reactor because then after the pre-treatment the hydrogenation reaction can be started by simply adding levulinic acid and no further temperature adjustment is required The hydrogenation reaction is preferably done in the presence of a second solvent. With 'second solvent' is meant that the first solvent may be a further, or different solvent than the solvent in which the pre-treatment is done (the 'first solvent'). The amount of second solvent is preferably low because the amount of solvent in the feed stream into the hydrogenation reactor is also preferably low. The less solvent in the feed, the more economical the process.

The feed stream preferably comprises levulinic acid and optionally (at least part of) the second solvent. The second solvent preferably comprises water. Preferably, the first solvent and the second solvent are the same. The concentration of a second solvent in feed stream is preferably 5 wt % or less. The concentration of GVL in the outlet is preferably at least 75 wt %, preferably the concentration of GVL is at least 80%, more preferably at least 83%. Most preferably the concentration of GVL in the outlet is 86 wt %. This is due to the reaction stoichiometry; every molecule of LA yields 1 molecule of GVL and one molecule of water. This means 86 wt % GVL and 14 wt % water. So if the (LA) feed comprised no water, the amount of water in the outlet would be at most 14 wt %. However, if the feed did contain water, the amount of water in the outlet could be higher.

The hydrogenation reaction is preferably done in a solvent comprising water, and the steady state concentration of water in the reactor is preferably between 13-20 wt %. If the amount of water is less than 14 wt % the conversion may be insufficient; if the amount of water is more than 20 wt % then there is may be too much water in the feed.

The hydrogenation reaction is preferably such that the conversion remains essentially the same without the need to adjust the temperature and/or residence time. The conversion is preferably stable for at least one day, preferably for at least two days, more preferably for at least three days, more preferably for at least a week, even more preferably for at least two weeks.

In an embodiment the conversion after 24 hours is at least 50%, more preferably the conversion is at least 60%, 70%. Even more preferably the conversion is at least 80%, 90%, even more preferably at least 95%, 98%, 99%.

In a further aspect the invention provides a method to stabilize a solid Ru catalyst for a hydrogenation reaction, said process comprising contacting the catalyst with a reductant in a solvent comprising water prior to the hydrogenation reaction.

In a further aspect the invention provides a solid Ru catalyst obtainable by the method of the invention. The catalyst may not be determined in terms of physical features, but is clearly different from solid Ru catalysts known in the art since they result in a stable repetitive batch or continuous hydrogenation reaction. The solid Ru catalyst obtainable by the method of the invention can be said to be a stabilized Ru catalyst.

EXAMPLES

Example 1

A batch reaction was carried out in a in stainless steel high pressure reactor (Premex Hastelloy steel-C, 160 mL, $p_{max}$=180 bar, $T_{max}$=250° C., 6-blade turbine with baffles, stirrer at 1000 rpm) equipped a hydrogen inlet was charged with Ru/C catalyst (5 wt %, Ru on activated carbon) and 80 g LA and 2 wt % water. The reactor was closed, and successively charged and depressurized with nitrogen (3 bar) three times and hydrogen (3 bar) three times. Upon the last charging with hydrogen the pressure was increased to 20 bars via a mass flow controller. The autoclave was heated to 130° C. which started the reaction. The reaction progress was monitored by taking in process samples. The samples were analyzed via GC to determine the levulinic acid conversion and the g-valerolactone yield. Entry 3 of Table 1 was analyzed for 4-hydroxypentanoic acid via NMR. The last sample was also analyzed via ICP-MS to determine the amount of Ru in the sample.

The reaction of Entry 1 was analyzed via ICP-MS to determine the (dissolved) Ru concentration with was 300 mg/kg in the reaction liquid. These examples show that the reaction is fast and efficient but Ru leaks, meaning that a continuous process is not possible since the catalyst will be continuously extracted from the reactor.

TABLE 1

Batch hydrogenation of LA with different Ru/C catalysts

| Exp | LA (g) | Catalyst type | catalyst (wet/g) | Water (g) | hydrogen pressure (bar) | T (° C.) | reaction time (min) | conversion LA (%) | yield GVL (%) | selectivity to VL (%) |
|---|---|---|---|---|---|---|---|---|---|---|
| 1 | 80 | Heraeus 5% Ru/C | 1.54 | 0.8 | 20 | 90 | 180 | 17.4 | 16.6 | 97.0 |
| 2 | 80 | Heraeus 5% Ru/C | 1.54 | 0.8 | 20 | 130 | 142 | 99.9 | 94.8 | 94.9 |
| 3 | 80 | ESCAT 4401 5% Ru/C | 0.8 | 0.8 | 20 | 130 | 240 | 99.9 | 97.0 | 97.0 |

Example 2

A batch reaction was carried out in a stainless steel high pressure reactor (Premex Hastelloy steel-C, 250 mL, $p_{max}$=180 bar, $T_{max}$=250° C., gas inducing stirrer) equipped with a hydrogen inlet, a liquid discharge equipped with a filter to prevent catalyst from leaving the reactor, and a high pressure feed vessel. The reactor was charged with 400 mg of Ru/TiO$_2$ catalyst (Johnsson Mathey 5 wt %) and 100 g GVL. The reactor was closed, and successively charged and depressurized with nitrogen (3 bar) three times and hydrogen (3 bar) three times. Upon the last charging with hydrogen the pressure was increased to 20 bars via a mass flow controller. The autoclave was heated to 110° C. After 60 minutes of pre-treatment 40 g LA (containing 1 wt % water) was introduced into the reactor via the high pressure feed vessel to start the reaction. The reaction progress was monitored by taking in-process samples were taken at 3, 5, 10, 15, 30, 45, 60, 90 and 1120 minutes. The samples were analyzed via GC to determine LA conversion and GVL yield. The last sample was also analyzed via ICP-MS to determine the amount of Ru in the sample.

The conversion reached completion after 120 minutes reaction time and the combined yield of GVL and 4-hydroxypentanoic acid was 99.9%. The concentration of Ru via ICP-MS was 16 mg/kg in the reaction liquid. These examples show that the reaction is fast and efficient but Ru leaks, meaning that a continuous process is not possible since the catalyst will be continuously extracted from the reactor.

Example 3

A continuous reaction was carried out in a stainless steel high pressure reactor (Premex Hastelloy steel-C, 250 mL, pmax=180 bar, Tmax=250° C., gas impelling stirrer) equipped a hydrogen inlet and a liquid (LA) feed. The reactor was charged with 1.0 g of Ru/TiO$_2$ catalyst (Johnsson Mathey 5 wt % Ru on TiO$_2$) and 100 g GVL. The reactor was closed, and successively charged and depressurized with nitrogen (3 bar) three times and hydrogen (3 bar) three times. Upon the last charging with hydrogen the pressure was increased to 20 bars via a mass flow controller with a hydrogen flow of 160 ml/h. The autoclave was heated to 110° C., and the catalyst pre-treatment was allowed to proceed for 60 minutes. After 60 minutes the reaction was started by continuous feeding of LA to the reactor at 2 mL/h. The pressure in the reactor was kept constant with a back pressure regulator at 20 bar hydrogen pressure and at a temperature of 110° C. Combined gas/liquid discharge from the reactor was done over a filter to keep the catalyst in the reactor. The height in which the filter is placed is adjustable to determines the hold-up in the reactor and the residence time. The reaction was monitored by taking in-process samples every hour. The samples were analyzed via GC to determine LA conversion and GVL yield.

The conversion profile shows an initial LA conversion but after 16 hours reaction time the levulinic acid entering the reactor leaves the reactor unaltered. No reaction takes place anymore. This could be due to e.g. leakage of inactivation.

Example 4

Figure 2:
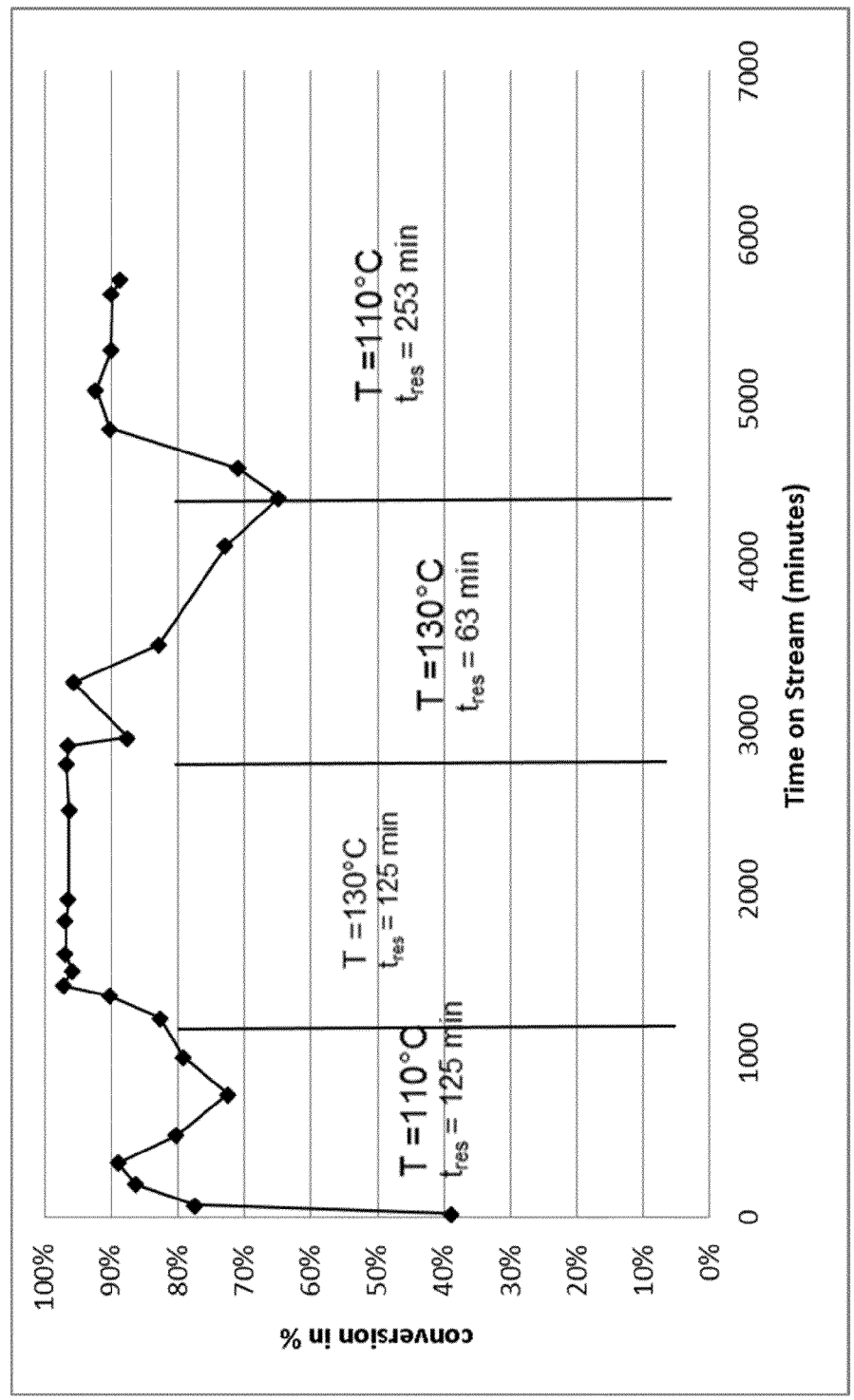

A continuous reaction was carried out in a stainless steel high pressure reactor (Premex Hastelloy steel-C, 250 mL, pmax=180 bar, Tmax=250° C., gas impelling stirrer) equipped with a hydrogen inlet, a liquid (LA) feed and a liquid discharge equipped with a filter to prevent catalyst from leaving the reactor. The reactor was charged with 2.51 g of Ru/C catalyst (Johnsson Mathey 5 wt % Ru on activated carbon) and 56.5 g water. The reactor was closed, and successively charged and depressurized with nitrogen (3 bar) three times and hydrogen (3 bar) three times. Upon the last charging with hydrogen the pressure was increased to 20 bars via a mass flow controller. The autoclave was heated to 110° C., and the catalyst pre-treatment was allowed to proceed for 60 minutes. After 60 minutes the reaction was started by continuous feeding of LA to the reactor at 0.5 mL/h, resulting in a residence time of tres=125 minutes. The pressure in the reactor was kept constant with a back pressure regulator at 20 bar hydrogen pressure and at a temperature of 110° C. Combined gas/liquid discharge from the reactor was done over a filter to keep the catalyst in the reactor. Temperature and residence time were adjusted in the course of the reaction as shown in FIG. 2. The reaction progress was monitored by taking in-process samples. The samples were analyzed via GC to determine LA conversion and GVL yield. A high and stable LA conversion was reached.

Example 5

A repetitive batch reaction was carried out in stainless steel high pressure reactor (Premex Hastelloy steel-C, 250 mL, $p_{max}$=180 bar, $T_{max}$=250° C., gas impelling stirrer) equipped a hydrogen inlet, a liquid discharge equipped with a filter to prevent catalyst from leaving the reactor, and a high pressure feed vessel. The reactor was charged with 450 mg of Ru/C catalyst (Johnsson Mathey 5 wt %, Ru on activated carbon) and 50.02 g GVL. The reactor was closed, and successively charged and depressurized with nitrogen (3 bar) three times and hydrogen (3 bar) three times. Upon the last charging with hydrogen the pressure was increased to 20 bars via a mass flow controller. The autoclave was heated to 110° C. After 60 minutes at reaction time and pressure 22 g LA (containing 5 wt % water) was introduced into the reactor via the high pressure feed vessel to start the reaction. The reaction was monitored by taking in-process samples. The samples were analyzed via GC to determine LA conversion and GVL yield. The last sample was also analyzed via ICP-MS to determine the amount of Ru in the sample.

After 120 minutes the reaction was stopped by discharging a percentage of the liquid from the reactor via the liquid discharge while the catalyst remained in the reactor under hydrogen.

Fresh LA was introduced again to the reactor via the high pressure feed vessel. The reaction was allowed to proceed for 120 minutes and a percentage of the liquid reactor content was again discharged. This procedure was repeated in total 5 times.

Results of the experiment are given in Table 2. The catalyst is dissolved and leaves the reactor via the liquid outlet and the reaction does not go to completion. Furthermore a fast de-activation is visible after two reactions.

TABLE 2

LA conversion of repetitive batch reaction with pretreatment of catalyst with GVL.

| Exp | LA (g) | Liquid out (%) | reaction time (min) | conversion LA (%) | Ru (mg/kg) |
|---|---|---|---|---|---|
| 1 | 19.9 | 47.2 | 120 | 68.8 | 20 |
| 2 | 19.3 | 52.5 | 120 | 67.5 | 6.4 |
| 3 | 48.2 | 52.4 | 120 | 44.6 | 3.8 |

Example 6

A repetitive batch reaction was performed in a stainless steel high pressure reactor (Premex Hastelloy steel-C, 250 mL, $p_{max}$=180 bar, $T_{max}$=250° C., gas impelling stirrer) equipped a hydrogen inlet, a liquid discharge equipped with a filter to prevent catalyst from leaving the reactor, and a high pressure feed vessel. The reactor was charged with 449 mg of Ru/C catalyst (Johnsson Mathey 5 wt %, Ru on activated carbon) and 50.24 g water. The reactor was closed, and successively charged and depressurized with nitrogen (3 bar) three times and hydrogen (3 bar) three times. Upon the last charging with hydrogen the pressure was increased to 20 bars via a mass flow controller. The autoclave was heated to 110° C. After 60 minutes 19.89 g LA (containing 5 wt % water) was introduced into the reactor via the high pressure feed vessel to start the reaction. The reaction was monitored by taking in-process samples. The samples were analyzed via GC to determine the LA conversion and GVL yield. The last sample was also analyzed via ICP-MS to determine the amount of Ru in the sample.

After 120 minutes the reaction was stopped by discharging a percentage of the liquid from the reactor via the liquid discharge while the catalyst remained in the reactor under hydrogen.

Fresh LA was introduced again to the reactor via the high pressure feed vessel. The reaction was allowed to proceed for 120 minutes and a percentage of the liquid reactor content was again discharged. This procedure was repeated in total 5 times.

Results of the experiment are given in Table 3. Virtually no Ru is leaving the reactor via the liquid outlet. Little de-activation is observed.

TABLE 3

LA conversion of repetitive batch experiment with pretreatment of catalyst in presence of water.

| Exp | LA in g | Liquid out (%) | reaction time (min) | conversion LA (%) | Ru (mg/kg) |
|---|---|---|---|---|---|
| 1 | 22.0 | 53 | 120 | 99.9 | $48 * 10^{-3}$ |
| 2 | 50.0 | 56 | 120 | 99.7 | $28 * 10^{-3}$ |
| 3 | 50.2 | 71 | 120 | 96.2 | $18 * 10^{-3}$ |
| 4 | 50.0 | 63 | 120 | 95.5 | $16 * 10^{-3}$ |
| 5 | 50.5 | 50 | 120 | 82.3 | $8 * 10^{-3}$ |
| 6 | 49.5 | — | 120 | 62.3 | $5 * 10^{-3}$ |

Example 7

A batch reaction was carried out in stainless steel high pressure reactor (Premex Hastelloy steel-C, 250 mL, pmax=180 bar, Tmax=250° C., gas impelling stirrer) equipped a hydrogen inlet, a liquid discharge equipped with a filter to prevent catalyst from leaving the reactor, and a high pressure feed vessel. The reactor was charged with 450 mg of Ru/C catalyst (Johnsson Mathey 5 wt % Ru on activated carbon) and either 50 g of water (pretreatment in water), or 20 g of GVL and 50 g of water (pretreatment in GVL/water), or 50 g of GVL (pretreatment in GVL). The reactor was closed, and successively charged and depressurized with nitrogen (3 bar) three times and hydrogen (3 bar) three times. Upon the last charging with hydrogen the pressure was increased to 20 bars via a mass flow controller. The autoclave was heated to 110° C. and the catalyst was pretreated for 60 minutes.

After 60 minutes either 20 g of LA and 20 g of GVL (pretreatment in water), or 20 g of LA (pretreatment in GVL/Water), or 20 g of LA and 20 g of water (pretreatment in GVL) were introduced into the reactor via the high pressure feed vessel to start the reaction. The reaction was monitored by taking in-process samples. The samples were analyzed via GC to determine LA conversion and GVL yield. The results are summarized in Table 4. See FIG. 1.

TABLE 4

LA conversion with pretreatment of catalyst in presence of different amounts of water

| Pretreatment in water | | Pretreatment in GVL/water (20/50) | | Pretreatment in GVL | |
|---|---|---|---|---|---|
| Time (min) | LA conversion (%) | Time (min) | LA conversion (%) | Time (min) | LA conversion (%) |
| 5 | 15.6 | 4 | 11.8 | 3 | 4.3 |
| 10 | 27.9 | 5 | 12.6 | 5 | 5.2 |
| 15 | 39.4 | 10 | 17.5 | 10 | 7.8 |
| 29 | 69.6 | 15 | 24.5 | 15 | 11.6 |
| 45 | 90.7 | 30 | 49.8 | 30 | 21.2 |
| 63 | 98.2 | 44 | 73.2 | 45 | 29.7 |
| 90 | 99.8 | 58 | 87.5 | 60 | 42.5 |
| 120 | 99.9 | 97 | 99 | 120 | 86.1 |
| | | 120 | 99.5 | | |

LEGEND TO THE FIGURES

FIG. 1. Reaction profile of Example 7, showing high yield in 4-HPA+GVL.

FIG. 2. Continuous hydrogenation of Example 4 with pretreatment with hydrogen in GVL, conversion vs time.

The invention claimed is:

1. A continuous or repetitive batch process for the hydrogenation of levulinic acid (LA) or esters thereof to at least gamma valerolactone (GVL) in a reactor comprising a feed stream and an outlet stream, in the presence of a solid Ru catalyst, the process comprising:
   (a) pretreating a solid Ru catalyst with hydrogen in the presence of a first solvent which comprises at least 5 wt. % water and at a pretreatment temperature of 350° or less to form a pretreated solid Ru catalyst; and
   (b) reacting levulinic acid (LA) with hydrogen and the pretreated solid Ru catalyst obtained in step (a) at a reaction temperature and residence time suitable to form at least gamma valerolactone (GVL).

2. The process according to claim 1, wherein the pretreatment temperature in step (a) is between 80° C. and 350° C.

3. The process according to claim 1, wherein step (a) and step (b) are carried out in the same reactor.

4. The process according to claim 1, wherein the first solvent is essentially free of GVL.

5. The process according to claim 1, wherein step (b) comprises reacting LA with hydrogen in the presence of a second solvent.

6. The process according to claim 5, wherein step (b) comprises supplying a feed stream comprised of LA and optionally at least part of the second solvent to a reactor.

7. The process according to claim 5, wherein the second solvent comprises water.

8. The process according to claim 5, wherein the first solvent and the second solvent are the same.

9. The process according to claim 6, wherein the second solvent is present in the feed stream in an amount of 5 wt % or less.

10. The process according to claim 9, wherein step (b) comprises reacting LA with hydrogen in the presence of water as the second solvent, and wherein the water has a steady state concentration in the reactor between 13-20 wt %.

11. The process according to claim 1, wherein the solid Ru catalyst is supported on C or $TiO_2$ 12. The process according to claim 2, wherein the pretreatment temperature in step (a) and the reaction temperature in step (b) is the same.

\* \* \* \* \*